United States Patent [19]

Renner et al.

[11] Patent Number: 5,002,864
[45] Date of Patent: Mar. 26, 1991

[54] COLOR PHOTOGRAPHIC RECORDING MATERIAL CONTAINING 2-EQUIVALENT MAGENTA COUPLERS

[75] Inventors: Günter Renner, Bergisch Gladbach; Werner Liebe, Leverkusen, both of Fed. Rep. of Germany

[73] Assignee: Agfa-Gevaert Aktiengesellschaft, Leverkusen, Fed. Rep. of Germany

[21] Appl. No.: 347,396

[22] Filed: May 4, 1989

[30] Foreign Application Priority Data

May 18, 1988 [DE] Fed. Rep. of Germany ....... 3816873

[51] Int. Cl.$^5$ ............................ G03C 1/10; G03C 7/32
[52] U.S. Cl. ........................................ 430/555; 430/554
[58] Field of Search ................................. 430/554, 555

[56] References Cited

U.S. PATENT DOCUMENTS

| | | | |
|---|---|---|---|
| 4,148,656 | 4/1979 | Fujiwhara et al. | 430/554 |
| 4,264,723 | 4/1981 | Ichijima et al. | 430/555 |
| 4,310,623 | 1/1982 | Watanabe et al. | 430/505 |
| 4,407,936 | 10/1983 | Ichijima et al. | 430/505 |
| 4,467,219 | 10/1984 | Sakanoue et al. | 430/542 |
| 4,584,266 | 4/1986 | Hirose et al. | 430/555 |

*Primary Examiner*—Charles L. Bowers, Jr.
*Assistant Examiner*—Janet C. Baxter
*Attorney, Agent, or Firm*—Connolly and Hutz

[57] ABSTRACT

Stable, color neutral images may be produced by a short time photographic process using a color photographic recording material containing at least one silver halide emulsion layer and at least one 2-equivalent magenta coupler corresponding to formula I on a (preferably reflective) layer support.

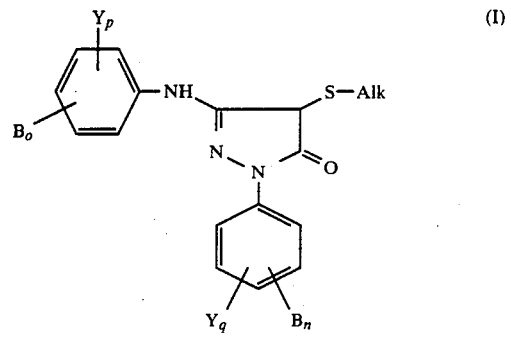

(I)

In the above formula,
B denotes a stabilizing group,
Y denotes halogen, alkoxy, alkyl, alkylsulphonyl, acylamino, alkoxycarbonyl, carbamoyl, sulphamoyl, amino, trifluoromethyl or cyano,
n and o stand for 0, 1 or 2 (but not both 0),
p stands for 0 or an integer $\leq 3-o$,
q stands for 0 or an integer $\leq 5-n$, and
Alk stands for alkyl which may be straight chained or branched and preferably has 1 to 22 carbon atoms and is optionally substituted, e.g. with hydroxy, alkoxy, aroxy or alkoxycarbonyl.

3 Claims, No Drawings

COLOR PHOTOGRAPHIC RECORDING MATERIAL CONTAINING 2-EQUIVALENT MAGENTA COUPLERS

This invention relates to a colour photographic recording material comprising at least one silver halide emulsion layer and at least one layer containing a 2-equivalent magenta coupler of a particular constitution. The recording material is particularly suitable for the production of colour images by a short time photographic process.

By short time photographic process is meant a process which is substantially shorter than conventional development processes and in which mainly the development time may be greatly reduced.

Whereas the development time in conventional processes at temperatures from 25 to 45° C. amounted to 3 minutes or more, the present invention relates to a process in which development carried out within the said temperature range is completed within a period of from 10 seconds to at the most 3 minutes. Development preferably takes less than 1 minute.

It is known to use pyrazolone compounds with unsubstituted 4-position of the pyrazolone ring (4-equivalent magenta couplers) as magenta couplers in colour photographic, light-sensitive recording materials. These compounds have, however, little colour producing effect and their stability is unsatisfactory, especially when they are stored under tropical conditions.

So-called 2-equivalent magenta couplers in which a substituent is introduced into the coupling position of a pyrazolone type coupler and split off as a fugitive group at the stage of colour development have been used for improving the colour producing effect. Couplers of this type are described, for example in U.S. Pat. No. 3 311 476, U.S. Pat. No. 3 419 391, U.S. Pat. No. 3 617 291 and U.S. Pat. No. 3 926 631. Other magenta couplers in which a substituent is attached to the coupling position by a sulphur atom are described in U.S. Pat. No. 3 214 437, U.S. Pat. No. 4 032 346, U.S. Pat. No. 3 227 554 and U.S. Pat. No. 3 701 783, JA 34044/78 and DE-A-29 44 601.

Chromogenic development converts 4-equivalent magenta couplers of the pyrazolone series into azomethine dyes which are rendered sufficiently stable for photographic recording materials by means of suitable known stabilizers such as derivatives of chroman, hydroquinone, piperidine, etc.

-S-Alkyl and -S-aryl fugitive groups attached to such couplers generally impair the light-resistance of the resulting azomethine dyes to such an extent that they cannot be used in photographic recording materials even when known stabilizers and light-protective agents are used. Exceptions are, for example, couplers of the type described in DE-A-36 22 007 and DE-A-31 31 926 which carry specially substituted thiophenols as fugitive groups.

Although the last-mentioned couplers give rise to dyes with sufficient stability to light, they cannot be used in photographic materials for short time processing because the formation of dyes from them is incomplete during the time of development. In addition, these couplers are unsuitable for reasons of cost because the synthesis of the fugitive groups required is complicated and cost intensive.

Moreover, many of the thio compounds released in the coupling reaction of such 2-equivalent couplers are not photographically harmless. They are liable to interfere with further development and inhibit the bleach fixing carried out after development. The latter can be recognized by a permanent Ag° image.

It is an object of the present invention to provide 2-equivalent magent couplers which 1. are usable for colour photographic materials viewed by reflected light, i.e.
   (a) give rise to dyes with suitable absorption properties,
   (b) have a high colour producing activity,
   (c) are highly stable both in dry and in moist heat,
   (d) have a high formaldehyde stability after development,
   (e) do not inhibit bleaching in bleach fixing baths, especially after prolonged use, and
   (f) form dyes which have excellent resistance both to dry and to moist heat and to the action of light,
2. contain groups which are readily accessible and rapidly split off in the coupling reaction with oxidized colour developers,
3. are comparatively unaffected by the usual changes in the pH of the colour developer and
4. enable the formation of dyes to be completed or at least to a sufficient extent for use in photographic materials by the time development in a short time process is terminated.

It has now been found that these aims can be realized by means of 2-equivalent magenta couplers having the structure shown below.

The present invention relates to a colour, photographic recording material having at least one silver halide emulsion layer and at least one layer containing a 2-equivalent magenta coupler corresponding to formula I

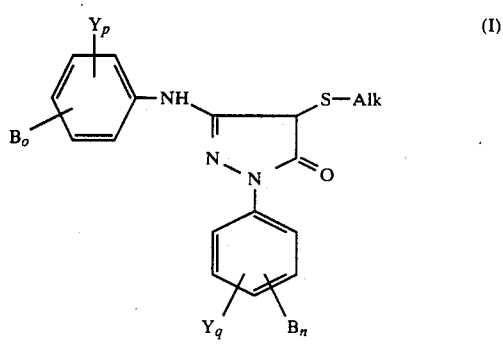

wherein

B denotes a stabilizing group,

Y denotes halogen, alkoxy, alkyl, alkylsulphonyl, acylamino, alkoxycarbonyl, carbamoyl, sulphamoyl, amino, trifluoromethyl or cyano, n and o stand for 0, 1 or 2 (but not both for 0).

p stands for 0 or an integer $<3-o$, q stands for 0 or an integer $<5-n$ and

Alk stands for a straight chained or branched alkyl preferably containing 1-22 carbon atoms, and optionally substituted, e.g. with hydroxy, alkoxy, aroxy or alkoxycarbonyl.

Acylamino is an acylated amino group in which acyl is derived from aliphatic or aromatic carboxylic or sulphonic acids, carbamic acids or carbonic acid semiesters. The term "acylamino" also includes cycloimido.

Carbamoyl and sulphamoyl include carbamoyl and sulph, amoyl groups which are monosubstituted or disubstituted on the N atom, e.g. with alkyl, aralkyl or aryl. Amino may similarly be monosubstituted or disubstituted or it may be a cyclic amino group (e.g. pyrrolidino, piperidino, or morpholino).

Alkyl groups in the alkylsulphonyl, acylamino, alkoxycarbonyl, carbamoyl and sulphamoyl may have 1 to 18 carbon atoms and are optionally branched and/or substituted.

Examples of suitable stabilizing groups B include compounds corresponding to the following formulae II, III and IV

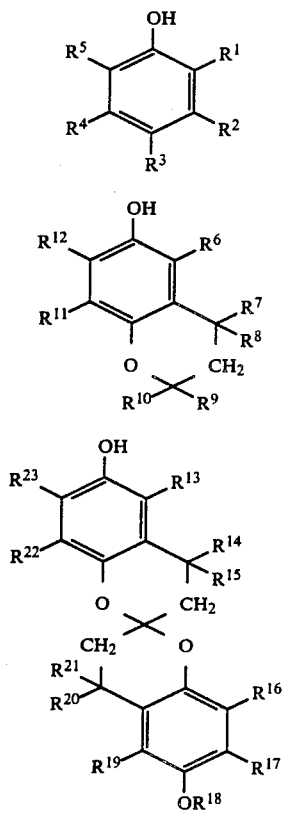

and their ethers which are attached by the OH group or one of the substituents $R^1$ to $R^{23}$ to the coupler molecule either by a direct bond or by a bridging member.

In formulae II to IV, the substituents have the following meanings:

$R^1$ to $R^5$ denote hydrogen, halogen, alkyl, alkoxy, aryl, aryloxy, carboxy, sulpho, alkoxycarbonyl, alkylamino, carbamoyl, sulphamoyl, alkylsulphonyl or arylsulphonyl $R^6$ to $R^{23}$ denote hydrogen or alkyl.

Halogen in particular denotes fluorine, chlorine or bromine.

Alkyl in particular denotes $C_1-C_{18}$-alkyl which is optionally branched.

Alkoxy in particular denotes $C_1-C_{12}$-alkoxy.

Acylamino in particular denotes $C_1-C_{18}$-alkylcarbonylamino, $C_1-C_{18}$-alkylsulphonylamino and $C_1-C_{18}$-alkoxycarbonylamino as well as benzoylamino and benzene sulphonylamino.

Alkoxycarbonyl in particular denotes $C_1-C_{18}$-alkoxycarbonyl.

Carbamoyl and sulphamoyl include carbamoyl and sulphamoyl groups which are mono-substituted or di-substituted on the nitrogen atom (e.g. with $C_1-C_2$-alkyl).

Aryl denotes in particular phenyl, aryloxy denotes in particular phenoxy and the phenyl ring may in each case be further substituted.

Bridging members may in particular be $C_1-C_{18}$-alkylenecarbonylamino groups.

Preferred 2-equivalent magenta couplers according to the present invention correspond to formula V

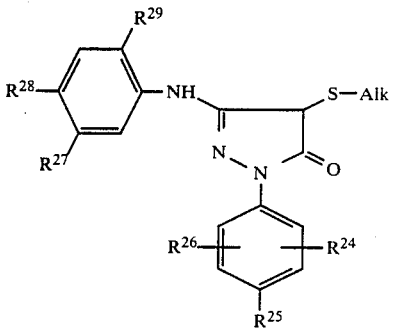

wherein
$R^{24}$ denotes chlorine,
$R^{25}$ denotes hydrogen, methoxy, chlorine, methyl, cyano or $B_1$,
$R^{26}$ denotes chlorine or methyl,
$R^{27}$ denotes hydrogen, di-$C_1-C_6$-alkylaminocarbonyl, $C_1-C_6$-alkylcarbonylamino or $B_1$,
$R^{28}$ denotes hydrogen, chlorine, CN or $B_1$,
$R^{29}$ denotes chlorine or methoxy, and either $R^{25}$ or $R^{27}$ or $R^{28}$ has the meaning of $B_1$ and
$B_1$ denotes a group corresponding to the following formula

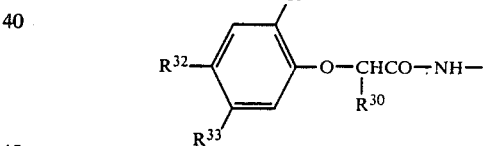

wherein
$R^{30}$ denotes hydrogen or $C_1-C_{12}$-alkyl,
$R^{31}$ denotes hydrogen, $C_1-C_8$-alkoxy, hydroxy, $C_1-C_8$-alkylcarbonyloxy or $C_1-C_8$-alkyl,
$R^{32}$ denotes hydrogen, hydroxy, $C_1-C_{12}$-alkoxy or $C_1-C_8$-alkyl and
$R^{33}$ denotes hydrogen or $C_1-C_8$-alkyl.

The substituents in formula V preferably have the following meanings:
$R^{24}$, $R^{25}$, $R^{26}$ and $R^{25}$: chlorine and
$R^{27}$: a group corresponding to the following formula

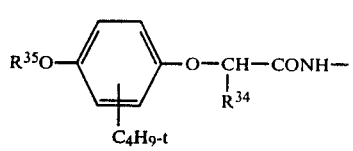

wherein $R^{34}$ and $R^{35}$ stand for hydrogen or $C_1-C_{12}$-alkyl.

The following are suitable groups of the structure
—S-Alk:
| | |
|---|---|
| —S—C$_8$—H$_{17}$ | A1 |
| —S—C$_{10}$H$_{21}$ | A2 |
| —S—C$_{12}$H$_{25}$ | A3 |
| —S—C$_{16}$H$_{33}$ | A4 |
| —C—(CH$_2$)$_3$—CO—OC$_4$H$_9$ | A5 |
| —S—CH(C$_4$H$_9$)—CO—OC$_6$H$_{13}$ | A6 |
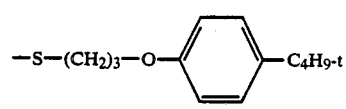 A7
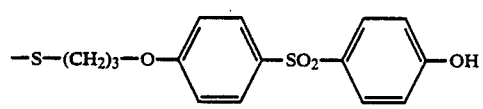 A8
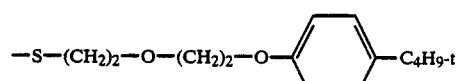 A9
| | |
|---|---|
| —S—(CH$_2$)$_4$—O—(CH$_2$)$_4$—S— | A10 |
| —S—(CH$_2$)$_2$—O—(CH$_2$)$_2$—O—C$_4$H$_9$ | A11 |
| —S—(CH$_2$)$_2$—O—C$_8$H$_{17}$ | A12 |
The following are examples of suitable groups B:
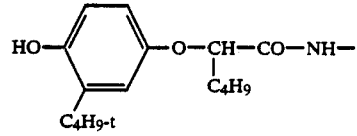 B1
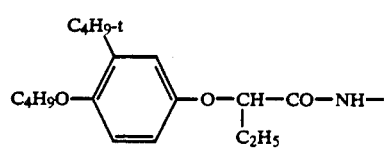 B2
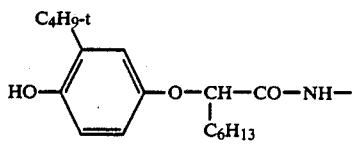 B3
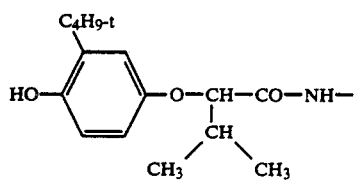 B4
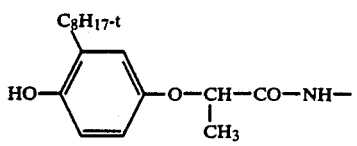 B5
-continued
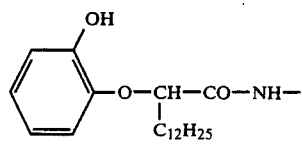 B6
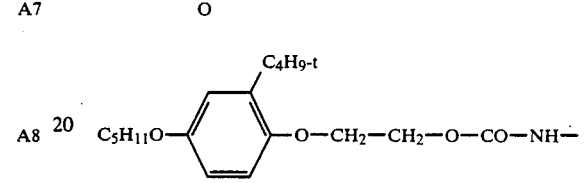 B7
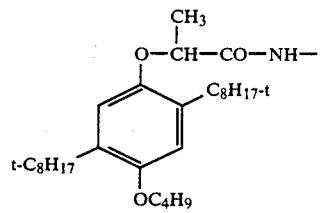 B8
B9
B10
B11
 B12
B13
B14

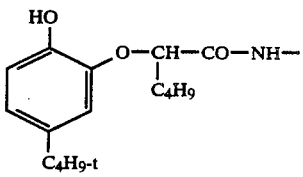
B15
The basic structure of the couplers may in particular correspond to the following formulae:
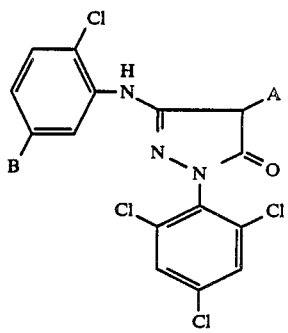
C1
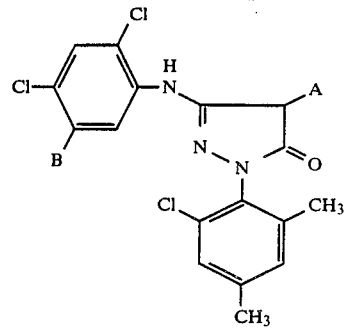
C5
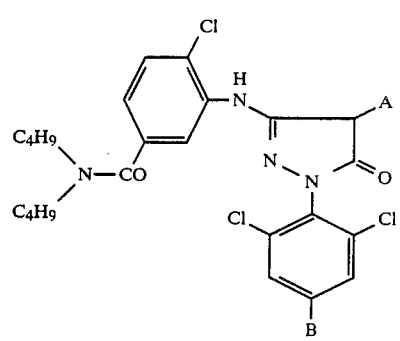
C6
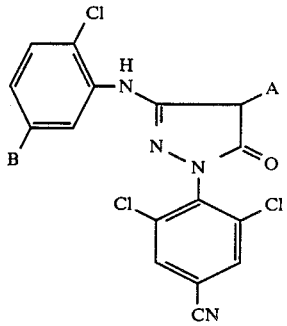
C7
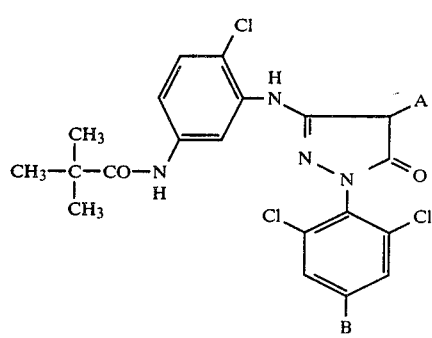
C8
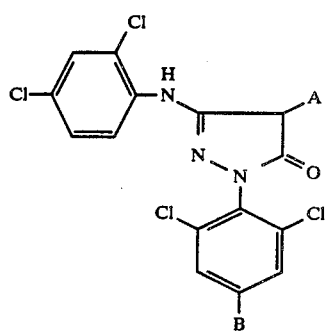
C4
The compounds entered in Table are particularly preferred couplers K.
| K | Fugitive group A | Stabilizing group | Basic Coupler structure |
|---|---|---|---|
| 1 | A1 | B1 | C1 |
| 2 | A1 | B13 | C1 |
| 3 | A2 | B14 | C1 |
| 4 | A3 | B1 | C1 |
| 5 | A3 | B2 | C8 |
| 6 | A3 | B3 | C1 |
| 7 | A3 | B10 | C3 |
| 8 | A3 | B13 | C1 |
| 9 | A4 | B1 | C4 |

-continued

| K | Fugitive group A | Stabilizing group | Basic Coupler structure |
|---|---|---|---|
| 10 | A4 | B4 | C5 |
| 11 | A4 | B13 | C1 |
| 12 | A5 | B6 | C2 |
| 13 | A5 | B13 | C7 |
| 14 | A6 | B1 | C4 |
| 15 | A6 | B3 | C6 |
| 16 | A6 | B8 | C1 |
| 17 | A6 | B13 | C4 |
| 18 | A7 | B14 | C1 |
| 19 | A7 | B15 | C7 |
| 20 | A8 | B2 | C8 |
| 21 | A8 | B14 | C7 |
| 22 | A9 | B1 | C4 |
| 23 | A10 | B1 | C1 |
| 24 | A10 | B13 | C1 |
| 25 | A11 | B13 | C6 |
| 26 | A12 | B1 | C4 |

The 2-equivalent magent couplers according to the invention are prepared by reaction of the corresponding 4-equivalent couplers with mercapto compounds by methods (or methods analogous thereto) described, for example, in U.S. Pat. No. 3 227 554, Research Disclosure 13806 (October 1975), DE-A-3 241 886, DE-A-3 622 007 and DE-A-3 644 406, for example as follows:

1. An alkylmercaptan or a corresponding disulphide is converted into a sulphenylhalide by means of a halogenating agent (for example, chlorine, bromine, sulphuryl chloride, N-bromosuccinimide, etc.) and then reacted with a 4-equivalent coupler in the presence of a catalyst. This method may also be carried out by the addition of a halogen (i.e. halogen in the form of a gas or a liquid) to a mixture of an alkylmercaptan phenol derivative or a 4-equivalent coupler (U.S. Pat. No. 3 227 554).

2. The active position of a 4-equivalent coupler is treated with a halogenating agent, optionally after previous protection of free amino groups by acylation (for example, insertion of an acetyl or an ethoxycarbonyl group), and the resulting compound is reacted with an alkylmercaptan in the presence of a basic catalyst or in the absence of a catalyst. The desired 2-equivalent coupler is obtained by removal of the protective group (JA-OS 91862/77).

The colour photographic recording material according to this invention may be processed in the usual manner by colour development, bleaching and fixing (or bleach fixing). Magenta dye images with excellent spectral and stability properties are obtained. The advantages of the colour photographic recording material according to the invention are particularly marked in so-called short time photographic processes, i.e. processes in which in particular the step of development, e.g. at temperatures from 25 to 45° C. takes no longer than 2 minutes, preferably not longer than 1 minute. The invention therefore also relates to a short time photographic process for the production of colour photographic images by chromogenic development followed by bleaching and fixing (or bleach fixing), using the colour photographic recording material described here. The processing steps following chromogenic development are advantageously also greatly reduced in time compared with those of conventional processes.

The colour photographic recording material according to the invention contains at least one light-sensitive silver halide emulsion layer, preferably a sequence of several such light-sensitive silver halide emulsion layers, optionally with light-insensitive layers of binder arranged between the said silver halide emulsion layers. According to the present invention, a 2-equivalent magenta coupler of formula I is associated with at least one of the light-sensitive silver halide emulsion layers present.

The halide present in the light-sensitive silver halide emulsions used in the light-sensitive layers may be chloride, bromide, iodide or mixtures thereof. The emulsions are preferably chloride-rich emulsions with a bromide content of less than 1 mol-%. Since materials containing such silver halide emulsions are particularly suitable for the short time photographic process, the present invention also relates to a colour photographic recording material having at least one light-sensitive silver halide emulsion layer in which more than 99% of the silver halide consists of silver chloride and with which a 2-equivalent magenta coupler of formula I and optionally also an oil former are associated.

The emulsions may be heterodisperse or monodisperse emulsions, preferably with an average grain size of from 0.3 μm to 1.2 μm. The silver halide grains may have a layered grain structure.

The emulsions may be chemically and/or spectrally sensitized in the usual manner and may also be stabilized with suitable additives. Suitable chemical sensitizers, spectral sensitizing dyes and stabilizers are described, for example, in Research Disclosure 17643 (December 1978): see in particular Chapters III, IV and VI.

The colour photographic recording material according to the invention preferably contains at least one light-recording silver halide emulsion layer for each of the three spectral regions, red, green and blue, which layer is spectrally sensitized by suitable sensitizing dyes in known manner.

A light-insensitive interlayer is generally arranged between layers which differ in their spectral sensitivity. This interlayer may contain substances for preventing accidental diffusion of developer oxidation products. When a material contains several silver halide emulsion layers of the same spectral sensitivity, these may be arranged adjacent to one another or they may be separated by a light-sensitive layer of a different spectral sensitivity (DE-A-19 58 709, DE-A-25 30 645, DE-A-26 22 922).

Colour photographic recording materials according to the invention normally contain colour couplers for producing the different partial colour images in cyan, magenta and yellow in spatial and spectral association with the silver halide emulsion layers of the different spectral sensitivities, the 2-equivalent magenta coupler according to the present invention being generally associated with a green-sensitive silver halide emulsion layer.

By "spatial association" is meant that the colour coupler is in such spatial relationship to the silver halide emulsion layer that they are capable of interacting to give rise to an imagewise correspondence between the silver image resulting from development and the colour image produced from the colour coupler. This is generally achieved by introducing the colour coupler into the silver halide emulsion layer or into an optionally light-insensitive layer of binder adjacent to said silver halide emulsion layer.

By "spectral association" is meant that the spectral sensitivity of each of the light-sensitive silver halide emulsion layers and the colour of the partial image produced from the spatially associated colour coupler are in a certain relationship to one another, each of the spectral sensitivities (red, green, blue) having a different colour of the corresponding partial colour image associated therewith (in general e.g. the colours cyan, magenta and yellow, in this sequence).

In preferred embodiments, therefore, red-sensitive silver halide emulsion layers have at least one non-diffusible colour coupler associated with them for producing the cyan partial colour image, generally a coupler of phenol or α-naphthol series, and green-sensitive silver halide emulsion layers have at least one non-diffusible colour coupler associated with them for producing the magenta partial colour image; for the latter, other magenta couplers, e.g. of the indazolone or pyrazoloazole series. may be used in addition to the 2-equivalent magenta couplers used according to the invention.

The blue-sensitive silver halide emulsion layers have at least one non-diffusible colour coupler associated with them for producing the yellow partial colour image, generally a colour coupler containing an open chain keto methylene group. Colour couplers of this type are known in large numbers and have been described in numerous Patent Specifications; see, for example, the publication "Farbkuppler" by W. PELZ in "Mitteilungen aus den Forschungslaboratorien der Agfa, Leverkusen/München", Volume III, page 111 (1961) and the publication by K.VENKATARAMAN in "The Chemistry of Synthetic Dyes", Vol.4. 341 to 387, Academic Press (1971).

Conventional layer supports may be used for the recording materials according to the invention, e.g. supports of cellulose esters such as cellulose acetate or of polyesters. Paper supports are also suitable, and these may be coated, e.g. with polyolefines, in particular with polyethylene or polypropylene; see Research Disclosure 17643, Chapter XVII. A light-reflective layer support is preferably used.

The protective colloids or binders used for the layers of the recording material may be any of the conventional hydrophilic film-forming substances, e.g. proteins, in particular gelatine. Casting auxiliaries and plasticizers may be used: see Research Disclosure 17643, Chapters IX, XI and XII.

The layers of the photographic material may be hardened in the usual manner, for example with hardeners containing at least two reactive oxirane, aziridine or acryloyl groups. The layers may also be hardened by the process according to DE-A-22 18 009. Further, the photographic layers or colour photographic multilayered materials may be hardened with hardeners of the diazine, triazine or 1,2-dihydroquinoline series or with vinylsulphone type hardeners. Other suitable hardeners are known from DE-A-24 39 551, DE-A-22 25 230 and DE-A-24 39 551 and from Research Disclosure 17643, Chapter X. The stabilizing effect of the oil formers according to the invention is particularly marked when hardeners which activate carboxyl groups are used, e.g. carbamoyl pyridinium salts or carbamoyl oxypyridinium salts.

In addition to the above-mentioned components, the colour photographic recording material according to the present invention may contain other additives, for example anti-oxidants, dye stabilizing agents and substances which influence the mechanical and electrostatic properties. It is also advantageous to use UV absorbent compounds in one or more of the layers of the recording material, preferably one of the upper layers, for the purpose of reducing or preventing the adverse effect of UV light on the colour images produced with the colour photographic material according to the invention. Suitable UV absorbents are described, for example. in U.S. Pat. No. 3 253 921. DE-C-2 036 719 and EP-A-0 057 160.

Other suitable additives are indicated in Research Disclosure 17643 and in "Product Licensing Index" of December 1971, pages 107-110.

Examples of suitable colour developer substances for the material according to the invention include in particular those of the p-phenylenediamine series, e.g. 4-amino-N,N-diethyl-aniline hydrochloride, 4-amino-3-methyl-N,N-diethyl-aniline hydrochloride, 4-amino-3-methyl-N-ethyl-N-β-(methanesulphonamido)-ethylaniline sulphate hydrate, 4-amino-3-methyl-N-ethyl-N-β-hydroxyethyl aniline sulphate, 4-amino-N-ethyl-N-(2-methoxyethyl)-m-toluidine-di-p-toluene sulphonic acid and N-ethyl-N-β-hydroxyethyl-p-phenylenediamine. Other suitable colour developers are described, for example, in J.Amer.Chem.Soc. 73, 3100 (1951). Suitable formulations for colour developers and additives for these developers are described, for example, in G. Haist, Modern Photographic Processing, 1979, John Wiley and Sons, New York, Vol.2, pages 545 et seq.

The colour developer bath used is preferably substantially free from benzyl alcohol and/or substantially free from bromide ions.

After colour development, the material is bleached and fixed in the usual manner. Bleaching and fixing may be carried out separately or together. The usual bleaching agent compounds are used, e.g. $Fe^{3+}$ salts and $Fe^{3+}$ complex salts such as ferricyanides, dichromates, water-soluble cobalt complexes, etc. Iron-III complexes of aminopolycarboxylic acids are particularly preferred, especially e.g. the complexes of ethylene diaminotetracetic acid, nitrilotriacetic acid, iminodiacetic acid, N-hydroxyethyl ethylene diaminotriacetic acid and alkyliminodicarboxylic acids and of the corresponding phosphonic acids. Persulphates are also suitable bleaching agents.

The material is generally washed after this development has been completed but effluent saving processes are known in which stabilizing baths are used instead of washing baths.

The process may also be rendered more rational by carrying the wash-water and the stabilizing bath in counter-current: see DE-A-29 20 222, DE-A-31 23 771, EP-A-0 182 566, EP-A-0 185 371, EP-A-0 186 158, EP-A-0 186 169, EP-A-0 186 504 and EP-A-206 148.

EXAMPLE 1

Colour photographic recording materials were prepared as described below.

(a) Preparation of the colour coupler emulsions 8 mmol of colour coupler are dissolved in equal parts by weight of dibutylphthalate and three times the quantity by weight of ethyl acetate in the presence of 0.15 g of sulphosuccinic acid dioctyl ester at a temperature of 50 to 75° C. The solution is then stirred into 150 g of a 7.5% by weight aqueous gelatine solution which is at a temperature of about 40° C.

(b) Preparation of the colour photographic recording materials which are to be tested The emulsion prepared under a) is mixed with a silver halide emulsion containing 8.2 g of silver in the form of silver bromide, 9.2 g of gelatine and 0.04 g of sodium dodecylbenzene sulphonate. The total volume is adjusted with water to 350 ml. The casting solution thus prepared is cast on a layer support of cellulose triacetate (0.8 g of Ag/m²).

(c) Processing and assessment

After drying, the material is exposed behind a graduated wedge and colour developed as follows:

1. Developer bath - 3.25 min 8,000 ml of distilled water, 47 g (N-ethyl-N-β-hydroxyethylamino)-2-merhyl aniline sulphate
25 g of hydroxyl ammonium sulphate
39 g of sodium sulphite
15.5 g of sodium bicarbonate
335 g of potassium carbonate
13.5 g of potassium bromide
made up to 10 l with distilled water; pH 10.

2. Bleach fixing bath - 1.5 min 35 ml of ammonia solution (28% by weight)
30 g of ethylene diaminotetracetic acid (EDTA),
15 g of Na₂SO₃,
100 g of ammonium thiosulphate,
60 g of sodium-(EDTA)-iron-III complex
made up to 1,000 ml with water, pH 7.

3. Washing - 3 min.

Table 1 shows the colour couplers used and the fresh sensitometric values obtained with these couplers.

The Table also shows in the last two columns the densities measured in percent in the blue and red spectral region at maximum density of the samples.

Comparison couplers

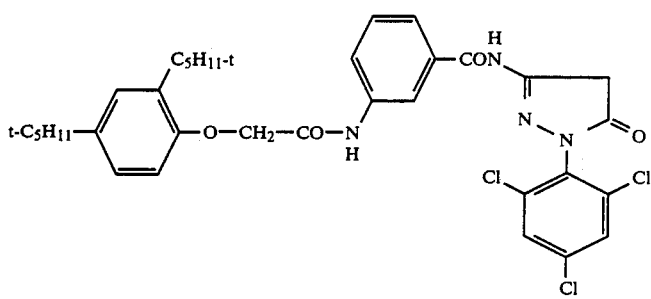

M-1

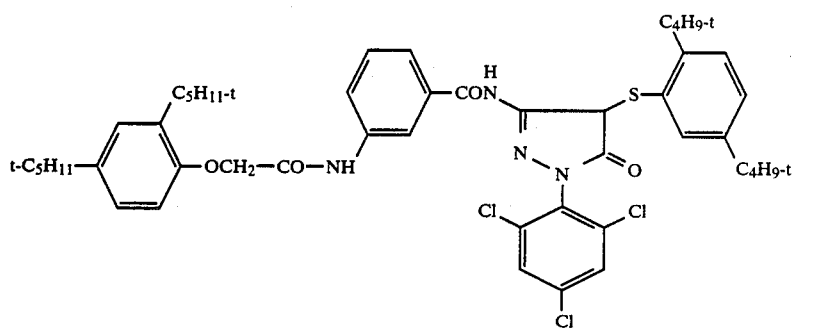

M-2

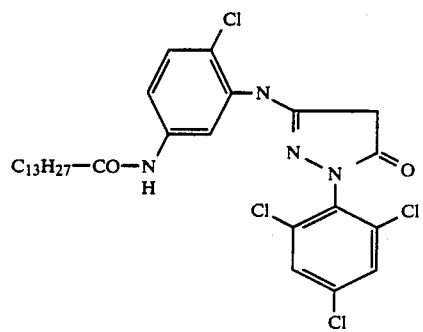

M-3

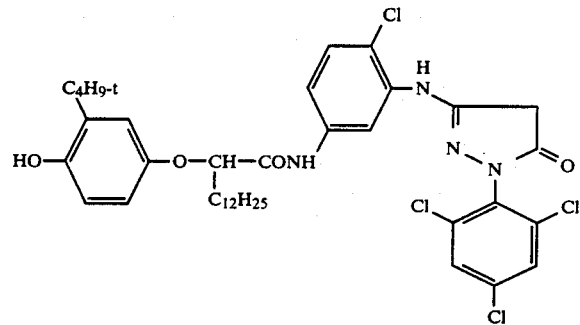

M-4

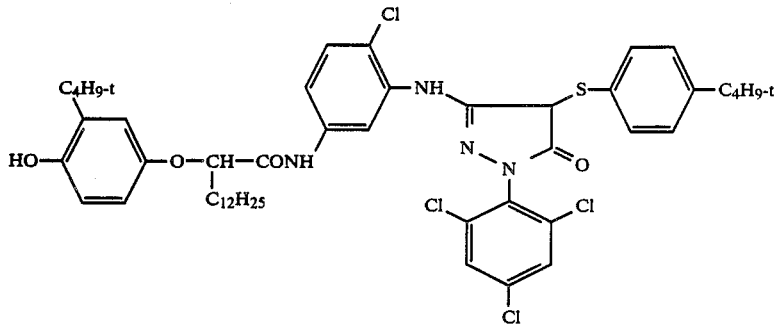

M-5

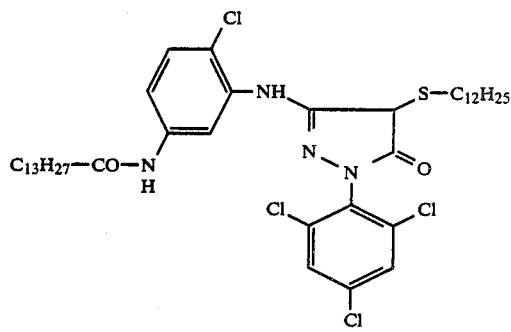

M-6

| Sample | Coupler | Sensitivity [DIN] | Colour yield | Gamma | % side density at $D_{max}$ blue | % side density at $D_{max}$ red |
|---|---|---|---|---|---|---|
| A | M-1 | 19.8 | 1.72 | 0.85 | 13 | 10 |
| B | M-2 | 17.2 | 1.18 | 0.53 | 14 | 9 |
| C | M-3 | 21.0 | 2.04 | 0.98 | 9 | 7 |
| D | M-4 | 20.6 | 1.96 | 0.93 | 10 | 10 |
| E | M-5 | 23.1 | 2.78 | 2.16 | 29 | 27 |
| F | M-6 | 23.2 | 3.40 | 2.45 | 10 | 8 |
| G | K-8 | 23.3 | 3.28 | 2.20 | 9 | 10 |
| H | K-11 | 23.7 | 3.18 | 2.12 | 10 | 9 |
| J | K-13 | 22.8 | 3.05 | 2.35 | 11 | 11 |
| K | K-18 | 23.2 | 3.10 | 2.20 | 9 | 10 |
| L | K-21 | 23.4 | 3.15 | 2.34 | 11 | 10 |
| M | K-26 | 22.9 | 2.95 | 2.18 | 13 | 12 |

Example 1 demonstrates the sensitometric advantages of 2-equivalent 3-anilinopyrazolone couplers (Samples E to M) compared with 2- and 4-equivalent 3-acylamino- and 4-equivalent 3-anilino-pyrazolone couplers. It also indicates the high colour yields and steep gradations of the couplers according to the invention but also of the Comparison couplers M-5 and M-6.

EXAMPLE 2

Samples C to M of Example 1 and Samples N to X (see below) were exposed with a grey wedge and developed as described below.

Samples N to X have the same composition as Samples C to M and in addition contain an emulsion which corresponds to the colour coupler emulsion but contains 8 mmol of stabilizer S-1 instead of the colour coupler.

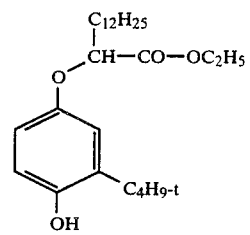

S-1

In addition, Samples Y (corresponding to C to M) and Z (corresponding to N to X) are prepared, Y containing Comparison coupler M-7 and Z containing Comparison coupler M-7 and in addition S-1:

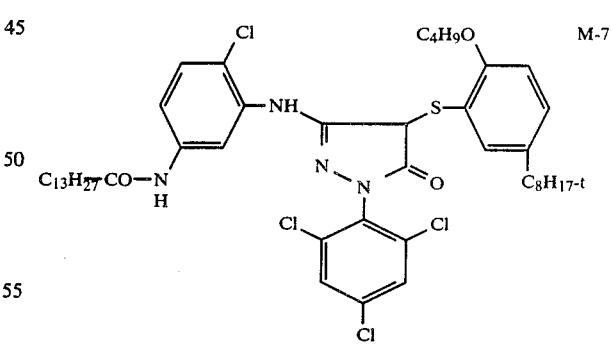

M-7

The samples obtained after Development 2 were measured in the fresh state and again after 4 weeks.

The samples obtained after Development 1 were covered with a UV protective foil and exposed to $7.2 \cdot 10^6$ $1 \times \cdot h$ in a Xenon test apparatus.

The results are summarized in Table 2.

Development 1 (E1)

(a) Colour developer $- 3.5$ min $= 33°$ C.

15 ml of benzyl alcohol 15 ml of ethylene glycol 3 g of hydroxylamine sulphate
4.5 g of 3-methyl-4-amino-N-ethyl-N-($\beta$)-methane sulphonamidoethyl)-aniline sulphate
32 g of $K_2CO_3$
2 g of $K_2SO_3$
0.6 g of KBr
1 g of the disodium salt of 1-hydrozyethane-1,1-diphosphonic acid
made up to 1,000 ml with water; pH 10.2.

(b) Bleach fixing bath - 1.5 min
35 ml of ammonia solution (28%)
30 g of EDTA
15 g of $Na_2SO_3$
100 g of ammonium thiosulphate
60 g of sodium-(EDTA)-iron-III complex
made up to 1,000 ml with water; pH 7.

(c) Washing - 3 min
Development 2 (E2)
(a) Colour developer - 45 g - 35° C.

| | |
|---|---|
| Triethanolamine | 9.0 g |
| N,N-Diethylhydroxylamine | 6.0 g |
| Diethyleneglycol | 0.05 g |
| 3-Methyl-4-amino-N-ethyl-N-methane sulphonamidoethyl-aniline sulphate | 6.0 g |
| Potassium sulphite | 0.2 g |
| Triethylene glycol | 0.05 g |
| Potassium carbonate | 22 g |
| Potassium hydroxide | 0.4 g |
| Disodium salt of ethylenediamino tetracetic acid | 2.2 g |
| made up with water to 1000 ml; pH 9.2 | |

(b) Bleach fixing bath - 45 s - 33° C.

| | |
|---|---|
| Ammonium thiosulphate | 75 g |
| Sodium hydrogen sulphite | 13.5 g |
| Ammonium acetate | 2.0 g |
| Ethylene diaminotetracetic acid (iron-ammonium salt) | 57 g |
| Ammonia (25%) | 9.5 g |
| Acetic acid | | c. Washing - 2 min—33° C.

TABLE 2

| Sample | E1 FA | E2 fresh FA | E2 fresh G2 | E2 4 weeks FA | E2 4 weeks G2 | % Reduction in Xenon test with UV protection $7.2 \cdot 10^6$ lx · h at D = 0.5 | 1.5 |
|---|---|---|---|---|---|---|---|
| C | 2.03 | 1.98 | 2.10 | 1.97 | 2.12 | 36 | 24 |
| D | 2.11 | 2.13 | 2.20 | 2.15 | 2.16 | 30 | 23 |
| E | 2.48 | 2.16 | 3.94 | 2.71 | 5.42 | 46 | 41 |
| F | 2.65 | 2.51 | 4.98 | 2.62 | 5.05 | 48 | 47 |
| G | 2.69 | 2.64 | 4.93 | 2.68 | 5.02 | 32 | 24 |
| H | 2.58 | 2.52 | 4.85 | 2.58 | 4.96 | 37 | 25 |
| J | 2.48 | 2.43 | 4.72 | 2.53 | 4.88 | 36 | 22 |
| K | 2.62 | 2.49 | 5.05 | 2.58 | 5.20 | 33 | 24 |
| L | 2.55 | 2.51 | 5.10 | 2.61 | 5.25 | 35 | 22 |
| M | 2.51 | 2.42 | 5.05 | 2.52 | 5.12 | 34 | 24 |
| N (C) | 2.08 | 2.05 | 2.15 | 2.06 | 2.14 | 22 | 16 |
| O (D) | 2.10 | 2.15 | 2.24 | 2.17 | 2.23 | 20 | 16 |
| P (E) | 2.32 | 1.98 | 3.74 | 2.45 | 4.95 | 36 | 30 |
| R (F) | 2.60 | 2.45 | 4.75 | 2.55 | 4.86 | 38 | 36 |

Example 2, Development 2, shows the sensitometric advantages of 2-equivalent pyrazolone couplers containing fugitive groups according to the invention compared with couplers containing arylthio fugitive groups It is seen that measured by the sensitometry, only the couplers according to the invention and Comparison coupler M-6 can be used in materials for short time photographic processes.

If one considers the light resistance of the dyes produced from these colour couplers by chromogenic development, it is clear that only the dyes produced from the colour couplers according to the invention have resistances to light equal to those obtained under comparable conditions from 4-equivalent couplers or from 2-equivalent couplers containing special arylthio fugitive groups (samples X,Y). It is also seen that the dyes obtained from the coupler M-6 (Sample F) which is not according to the invention cannot achieve the level of stability to light of the couplers according to the invention even when stabilizer S-1 (Sample R) is added. The same also applies to other stabilizers known in the art.

Summarizing Example 2 shows that in materials for short time processing, only the 2.equivalent couplers according to the invention may be used by virtue of their sensitometric properties and the stability of their dyes to light.

EXAMPLE 3

A coupler emulsion containing the 4-equivalent magenta coupler M-3 in a quantity providing a ratio by weight of $AgNO_3$/coupler of 1:0.9 is added to a green-sensitized and stabilized AgCl emulsion having a silver nitrate/gelatine ratio of 1:1.

To prepare the coupler emulsion, 4 g of gelatine were dissolved in 50 ml of water and to this solution was added 0.5 g of dodecylbenzenesulphonate An oil phase consisting of 10 g of coupler M-3, 4 g of stabilizer S.2 and 2 g of stabilizer S-3, 4 g of tricresylphosphate and 3.5 g of dinonylphthalate dissolved in 20 ml of ethyl acetate was emulsified in this solution by means of a high speed stirrer with a powerful shearing action. 2.06 g of gelatine (as 10% solution) was then added to the emulsion per 1 g of $AgNO_3$ and the emulsion was diluted with water so that 1,000 ml of emulsion contained 12.5 g of $AgNO_3$. The emulsion was then applied in a wet layer thickness of 36 μm to a paper which was coated with polyethylene on both sides.

Another layer, containing 1 g of gelatine per m² and containing the hardener CAS Reg. No 65411-60-1 in a quantity of 5% by weight, based on the total quantity of gelatine, was also applied The resulting material was cut up and exposed behind a $\sqrt[4]{2}$ step wedge. Development was carried out as described in Example 2, Development 2.

Step wedges were also prepared similarly with couplers M-6, M.8, M-9 and the coupler according to the invention K-8.

The following values (Table 3) were obtained from measuring the sensitivity E (D =0.6) and shoulder gradation $G_2$ and maximum density $D_{max}$ immediately after development:

TABLE 3

| Coupler | E | G | $D_{max}$ |
|---|---|---|---|
| M-3 | 1.74 | 3.04 | 2.50 |
| M-6 | 1.68 | 4.82 | 2.35 |
| M-8 | 1.78 | 4.54 | 1.71 |
| K-8 | 1.66 | 4.93 | 2.33 |

The following values were measured (Table 4) after the developed wedges had been stored for 1 week/2 weeks:

TABLE 4

| Coupler | E | $G_2$ | $D_{max}$ |
|---|---|---|---|
| M-3 | 1.74/1.74 | 3.04/3.03 | 2.50/2.50 |
| M-6 | 1.68/1.68 | 4.89/4.89 | 2.49/2.50 |
| M-9 | 1.80/1.80 | 5.49/5.49 | 2.45/2.44 |
| K-8 | 1.66/1.66 | 4.97/4.97 | 2.51/2.50 |

Comparison couplers M-8 and M-9 show too great a sensitometric change in storage. Comparison coupler M-6, which only shows a small sensitometric change, must be eliminated on account of its very poor dye stability.

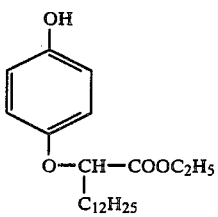

S-2

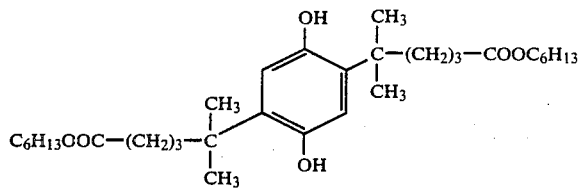

S-3

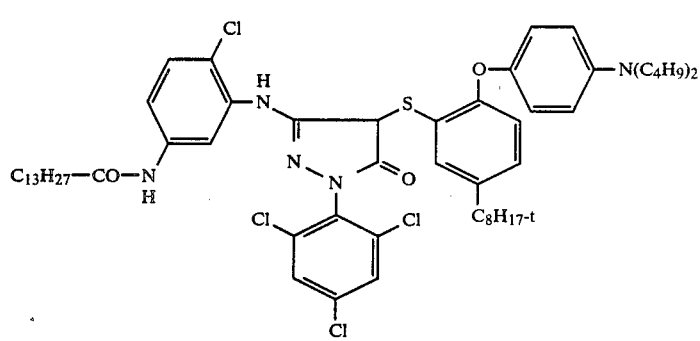

M-8

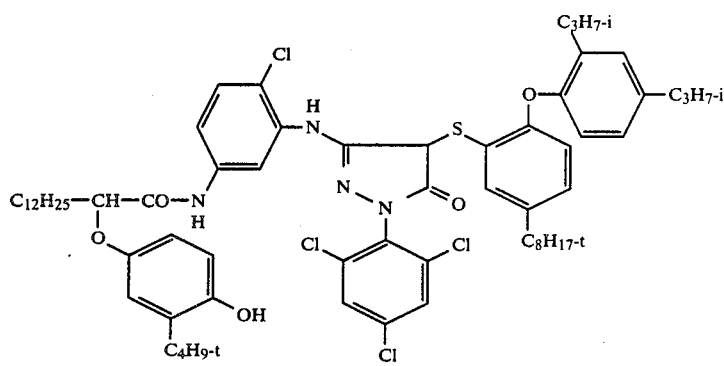

M-9

The wedges are then exposed behind a UV filter in a Xenotest apparatus at $10 \times 10^6 \, lx \cdot h$. The following values were obtained for the percentage reduction in density for density 1.1:

| | |
|---|---|
| M-3 | −23% |
| M-6 | −57% |
| M-8 | −21% |
| M-9 | −31% |
| K-8 | −27%. |

The results show that only coupler K-8 according to the invention may be used as 2-equivalent coupler for short time processing. The steep gradation is very marked compared with the 4-equivalent coupler M-3.

EXAMPLE 4

The following layers were applied to a layer support of paper which was coated with polyethylene on both sides. The quantities are based on 1 m².

1. A substrate layer of 200 mg of gelatine with the addition of $KNO_3$ and chrome alum 2. A blue-sensitive silver chloride emulsion layer of 600 mg of $AgNO_3$ containing 2,100 mg of gelatine, 1.1 mmol of yellow coupler, 27.7 mg of 2,5-dioctylhydroquinone and 1,200 mg of tricresylphosphate 3. An interlayer of 1,300 mg of gelatine, 80 mg of 2,5-dioctylhydroquinone and 100 mg of tricresylphosphate 4. A green-sensitive silver chloride emulsion layer of 530 mg of $AgNO_3$ containing 750 mg of gelatine, 0.625 mmol of the magenta coupler shown in Table 3 below 118 mg of α(3-t-butyl-4-hydroxyphenoxy)-myristic acid ethyl ester, 43 mg of 2,5-dioctylhydroquinone and oil former as shown in Table 3, 5. An interlayer of 1550 mg of gelatine, 285 mg of the UV absorbent Tinuvin 343 ®,k 80 mg of dioctylhydroquinone and 650 mg of tricresylphosphate, 6. A red-sensitive silver halide emulsion layer of 400 mg of AgNO3 containing 1470 mg of gelatine, 0.780 mmol of cyan coupler, 285 mg of dibutylphthalate and 122 mg of tricresylphosphate, 7. A protective layer of 1200 mg of gelatine and 134 mg of Tinuvin 343 ® and 8. A hardening layer of 400 mg of gelatine and 400 mg of an instant hardener [CAS REg. No. 65411-60-1].

The following couplers were used in layers 2 and 6:

sity range, i.e. no colour change was found at the transition to higher densities.

A different result was obtained from short time processing. At very low densities, the samples were again found to be neutral grey. With increasing density, however, materials 3 and 4 tipped over and in the region of maximum colour density they were bright green. It was only after several days' storage at room temperature or 2 hours' storage at 65° C. that these materials were also neutral in colour.

The other materials, i.e. materials 1 and 2 (4-equivlent couplers) and materials 5 to 10 (2-equivalent couplers) containing small amounts of silver and coupler were found to be neutral grey after processing.

Materials 3 and 5 differed from all the other materials in their poor bleaching response when exposed (as in Example 2); the grey wedges underwent discolouration Yellow coupler

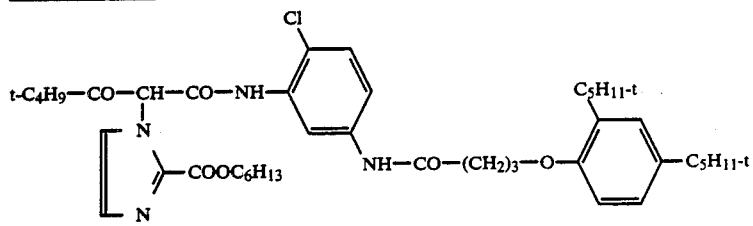

Cyan coupler

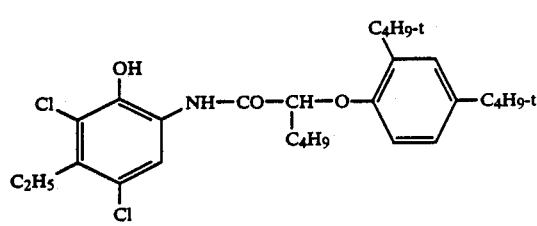

The quantities of coupler and silver halide in layer 4 are applicable when the magenta coupler is a 4-equivalent coupler. When a 2-equivalent magenta coupler is used, it is applied in a quantity of 0.5 mmol and the quantity of silver chloride applied corresponds to 420 mg of AgNO3.

Various recording materials differing only in layer 4 were prepared, as shown in Table 3 below:

TABLE 3

| Material | Magenta coupler |
|---|---|
| 1 | M-3 |
| 2 | M-4 |
| 3 | M-5 |
| 4 | M-7 |
| 5 | M-6 |
| 6 | K-4 |
| 7 | K-8 |
| 8 | K-13 |
| 9 | K-16 |
| 10 | K-26 |

The materials were exposed behind a grey wedge and developed by both development processes (Development 1 and Development 2) described in Example 2.

When long time processing was employed, all the materials were found to be neutral over the whole den-after some time and turned a dirty green.

We claim:

1. Colour photographic recording material having at least one silver halide emulsion layer arranged on a layer support and at least one layer containing a 2-equivalent magenta coupler corresponding to formula V

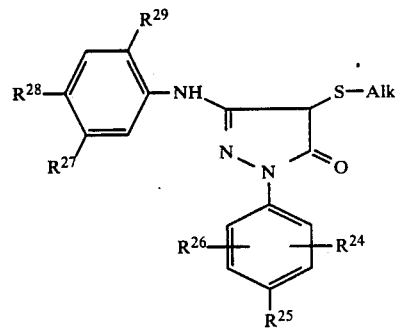

wherein
Alk denotes straight chained or branched alkyl or straight chained or branched alkyl substituted with hydroxy, alkoxy, aroxy or alkoxycarbonyl;
$R^{24}$ denotes chloro;
$R^{25}$ denotes hydrogen, methoxy, chloro, methyl, cyano or $B_1$;
$R^{26}$ denotes chloro or methyl;
$R^{27}$ denotes hydrogen, di-$C_1$-$C_6$-alkylaminocarbonyl, $C_1$-$C_6$-alkylcarbonylamino or $B_1$;
$R^{28}$ denotes hydrogen, chloro, CN or $B_1$;
$R^{29}$ denotes chloro or methoxy and either $R^{25}$ or $R^{27}$ or $R^{28}$ has the meaning of $B_1$ and
$B_1$ denotes a residue of the formula

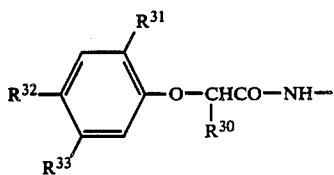

wherein $R^{30}$ denotes hydrogen or $C_1$–$C_{12}$-alkyl;

$R^{31}$ denotes hydrogen, $C_1$–$C_8$-alkoxy, hydroxy, $C_1$–$C_8$-alkylcarbonyl or $C_1$–$C_8$-alkyl;

$R^{32}$ denotes hydroxy or $C_1$–$C_{12}$-alkoxy and $R^{33}$ denotes hydrogen or $C_1$–$C_8$-alkyl.

2. Recording material according to claim 1, characterised in that more than 99 mol-% of the silver halide in the silver halide emulsion layer containing the 2-equivalent magenta coupler is silver chloride and less than 1 mol-% is silver bromide.

3. Recording material according to claim 2 characterised in that the layer support is a reflective layer support.

* * * * *